United States Patent [19]
Itano et al.

[11] Patent Number: 6,162,908
[45] Date of Patent: Dec. 19, 2000

[54] POLYPEPTIDE OF HUMAN-ORIGIN HYALURONATE SYNTHETASE AND DNA ENCODING THE SAME

[75] Inventors: Naoki Itano, Owariasahi; Koji Kimata, Nagoya, both of Japan

[73] Assignee: Seikagaku Corporation, Japan

[21] Appl. No.: 09/155,768

[22] PCT Filed: Mar. 31, 1997

[86] PCT No.: PCT/JP97/01111

§ 371 Date: Oct. 5, 1998

§ 102(e) Date: Oct. 5, 1998

[87] PCT Pub. No.: WO97/38113

PCT Pub. Date: Oct. 16, 1997

[30] Foreign Application Priority Data

Apr. 5, 1996 [JP] Japan ................................ 8-084326
Apr. 30, 1996 [JP] Japan ................................ 8-109663

[51] Int. Cl.[7] ........................ C12N 9/26; C12N 9/00
[52] U.S. Cl. ........................ 536/23.2; 435/6; 435/69.1; 435/183; 536/23.1
[58] Field of Search ........................ 435/201, 69.1, 435/6, 183; 536/23.1, 23.2

[56] References Cited

FOREIGN PATENT DOCUMENTS

WO 98/00551  1/1998  WIPO.

OTHER PUBLICATIONS

Gibco BRL/Life Technologies Catalogue 1993–1994, p. 7—7, 1993.

Andrew P. Spicer, et al., Molecular Cloning and Characterization of a Putative Mouse Hyaluronan Synthase, The Journal of biological Chemistry vol. 217, No. 38, pp. 23400–23406, Sep. 20, 1996.

Andrew P. Spicer, et al., Molecular cloning and Characterization of a cDNA Encoding the Third Putative Mammalian Hyaluronan Synthase, The Journal of Biological Chemistry, vol. 272, No. 14, pp. 8957–8961, Apr. 4, 1997.

Naoki Itano, et al., Expression Cloning and Molecular Characterization of HAS Protein, a Eukaryotic Hyaluronan Synthase, The Journal of Biological Chemistry vol., 271, No. 17, pp. 9875–9879, Apr. 26, 1998.

Naoki Itano, et al., Molecular Cloning of Human Hyaluronan Synthase, Biochemical and Biophysical Research Communications, vol. 222, No, 3, pp. 816–821, May 24, 1996.

Ann M. Shyjan, et al., Functional Cloning of the CDNA for a Human Hyaluronan synthase, The Journal of Biological Chemistry Vo. 271, No. 38, pp. 23395–23399, Sep. 20, 1996.

*Primary Examiner*—Rebecca E. Prouty
*Assistant Examiner*—Richard Hutson
*Attorney, Agent, or Firm*—Knobbe Martens Olson & Bear, LLP

[57] ABSTRACT

A DNA encoding at least part of a hyaluronan synthase of human origin, particularly encoding the whole or a part of an amino acid sequence shown by SEQ ID NO: 4. A polypeptide of the hyaluronan synthase of human origin, which is encoded by the DNA, may have a substitution, deletion or insertion of one or more amino acid residues that does not substantially lower an activity of synthesizing hyaluronan. A polypeptide of the hyaluronan synthase of human origin or a part thereof encoded by the DNA is also provided.

6 Claims, No Drawings

POLYPEPTIDE OF HUMAN-ORIGIN HYALURONATE SYNTHETASE AND DNA ENCODING THE SAME

TECHNICAL FIELD

The present invention relates to a polypeptide of a hyaluronan synthase of human origin and a DNA encoding the same.

BACKGROUND ART

Hyaluronan is one of high molecular weight glycosaminoglycans and is constituted by repeated β-1,4 linked disaccharide units, each of the unit being composed of glucuronic acid linked to N-acetylglucosamine by a β-1,3 bond (GlcUAβ1-3GlcNAc; GlcUA and GlcNAc represent glucuronic acid and N-acetylglucosamine, respectively). Hyaluronan is a characteristic constituent of the extracellular matrix at the early stage of morphogenesis of animals. Its synthesis is regulated spatially and temporally (Toole, B. P. (1981) Cell Biology of the Extracellular Matrix (Hey, E. D., ed.) pp. 259–294, Plenum, New York). Accumulation of hyaluronan on the cell surface is correlated with regulation of behavior of cells, particularly migration, adhesion, cure of wounds, infiltration of tumors, and the like (Turley, E. A. (1989) The Biology of Hyaluronan, Ciba Foundation Symposium 143, pp. 121–137; Wiley, Chichester, England; Knudson, W., Biswas, C., Li, X.-Q., Nemec, R. E., and Tool, B. P. (1989) The Biology of Hyaluronan, Ciba Foundation Symposium 143, pp. 150–169, Wiley, Chichester, England; Laurent, T. C., and Fraser, J. R. E. (1992) FASEB J. 6, 2397–2404; Kimata, K., Honma, Y., Okayama, M., Oguri, K., Hozumi, M., and Suzuki, S. (1983) Cancer Res. 43, 1347–1354).

Biosysthesis of hyaluronan has been widely studied using a procaryote, Streptococci. A recent report revealed that a structural gene of hyaluronan synthase derived from *Streptococcus pyogenes* which is a procaryote was isolated (DeAngelis, P. L., Papaconstantinou, J., and Weigel, P. H. (1993) J. Biol. Chem. 268, 19181–19184). In contrast, little is known about the biosynthesis mechanism of hyaluronan in eucaryotes. Attempts have been made to purify eucaryotic hyaluronan synthase. However, some reports showed that the obtained enzyme lost its activity (Mian, N. (1986) Biochem. J. 237, 343–357; Ng, K. F., and Schwartz, N. B. (1989) J. Biol. Chem. 264, 11776–11783; Klewes, L., Turley, E. A., and Prehm, P. (1993) Biochem. J. 290, 791–795). Any DNA encoding a polypeptide of eucaryotic hyaluronan synthase is not known.

If a polypeptide of hyaluronan synthase derived from eucaryotes, particularly human, and a DNA encoding it are obtained, they would be useful for treatments, including gene therapy, of diseases caused by decreased expression of hyaluronan in humans. In addition, these substances would also be useful for gene therapy for suppressing metastasis of cancer using an antisense DNA, RNA, or the like as well as development of hyaluronan synthase-specific inhibitors.

DISCLOSURE OF THE INVENTION

The object of the present invention is to provide a polypeptide of a hyaluronan synthase of human origin and a DNA encoding the polypeptide.

The present inventors intensively investigated to achieve the above object and, as a result, succeeded in cloning a cDNA encoding a polypeptide of hyaluronan synthase, which has hyaluronan synthase activity, from cells of an organism except human and, by using a fragment derived from the cDNA, cloning a cDNA encoding a polypeptide of a hyaluronan synthase of human origin. Thus, the present invention was completed.

The present invention provides a DNA encoding the following polypeptide (a) or (b):

(a) a polypeptide of a hyaluronan synthase of human origin; and (b) a partial polypeptide of the polypeptide (a).

Further, the present invention also provides a DNA encoding any one of the following polypeptides (a) to (c):

(a) a polypeptide having the amino acid sequence shown by SEQ ID NO: 4;

(b) a polypeptide having the amino acid sequence shown by SEQ ID NO: 4, which has a substitution, deletion or insertion of one or more amino acid residues that does not substantially lower an activity of synthesizing hyaluronan; and (c) a partial polypeptide of the polypeptide (a) or (b).

The above-described DNA preferably encodes the whole or the amino acid sequence shown by SEQ ID NO: 4. It also preferably has at least a part of the nucleotide sequence shown by SEQ ID NO: 1, more preferably has a nucleotide sequence of from position 149 to position 1777 of the nucleotide sequence shown by SEQ ID NO: 1. In the present invention, the DNA of the present invention includes a DNA or an RNA complementary to the DNA.

Furthermore, the present invention provides a polypeptide of a hyaluronan synthase of human origin or a part thereof (hereinafter referred to "the polypeptide of the present invention") encoded by the above-described DNA of the present invention.

The term "part of the polypeptide" used herein means a part having an activity or function such as hyaluronan synthase activity and immunogenicity, or a part, the nucleotide sequence of which is specific to the hyaluronan synthase and can be used as a primer or a probe.

Further, the term "at least part of the nucleotide sequence" used herein means a part encoding a part of the polypeptide having an activity or function such as hyaluronan synthase activity and immunogenicity, or the part which is specific to the hyaluronan synthase and can be used as a primer or a probe.

The following explains the embodiments of the present invention in detail.

I. THE DNA OF THE PRESENT INVENTION

The DNA of the present invention is the one encoding at least part of a polypeptide of a hyaluronan synthase of human origin, specifically one encoding at least part of a polypeptide having the amino acid sequence shown by SEQ ID NO: 4. The polypeptide of the hyaluronan synthase of human origin or the polypeptide having the amino acid sequence shown by SEQ ID NO: 4, which is encoded by the DNA of the present invention, may have a substitution, deletion or insertion of one or more amino acid residues that does not substantially lower the activity of synthesizing hyaluronan. The DNA of the present invention is preferably a DNA encoding at least part of the polypeptide of a hyaluronan synthase of human origin, and encoding the whole or a part of the amino acid sequence shown by SEQ ID NO: 4, or a DNA encoding at least part of the polypeptide of the hyaluronan synthase of human origin, which has the amino acid sequence shown by SEQ ID NO: 4, in which a substitution, deletion or insertion of one or more amino acid residues that does not substantially lower the activity of synthesizing hyaluronan may be present. More preferably, the DNA of the present invention is a DNA encoding the whole of the amino acid sequence shown by SEQ ID NO: 4. The DNA of the present invention is still more preferably a DNA having at least part of the nucleotide sequence shown by SEQ ID NO: 1. A specific example of the DNA is one having the nucleotide sequence of from position 149 to position 1777 of the nucleotide sequence shown by SEQ ID NO: 1. The DNA of the present invention may have a substitution, deletion, or insertion of one or more nucleotides as long as it has substantially the same nucleotide sequence as shown by SEQ ID NO: 1 and does not substantially lower the hyaluronan-synthesizing activity of the polypeptide of hyaluronan synthase encoded by the above nucleotide sequence. In other words, the DNA of the present invention includes DNA encoding a polypeptide of hyaluronan synthase having the above-described substitution, deletion, or insertion of nucleotide(s).

A specific example of the DNA of the present invention is a DNA having the nucleotide sequence of from position 149 to position 1777 of the nucleotide sequence shown by SEQ ID NO: 1. One of ordinary skill in the art would readily understand that the DNA of the present invention include DNAs having the nucleotide sequences different from that as described above due to degeneracy of the genetic codes.

Also, the DNA of the present invention may be either a coding single strand encoding only the polypeptide of hyaluronan synthase or a double-stranded chain composed of the above single strand and a DNA strand having complementary sequence thereto.

Since the nucleotide sequence of the DNA of the present invention was revealed by the present invention, the DNA can be synthesized based on the sequence. The DNA is also obtained by amplifying the DNA of the present invention from human chromosomal DNA or mRNA by polymerase chain reaction (PCR) method using oligonucleotide primers prepared based on the sequence. The DNA of the present invention was obtained for the first time by the cDNA cloning comprising the following steps as also described in the example below.

(1) Cloning of a cDNA Encoding a Polypeptide of a Hyaluronan Synthase of Mouse Origin:
i) selection of mouse cells capable of high level production of hyaluronan and preparation of mouse mutant cells deficient in hyaluronan-synthesizing ability;
ii) isolation of a poly(A)$^+$ RNA containing an mRNA corresponding to the polypeptide of hyaluronan synthase;
iii) construction of a mouse cDNA library;
iv) introduction of the cDNA library constructed in iii) into the mutant cells deficient in hyaluronan-synthesizing ability prepared in i) (transfection);
v) selection of cells capable of synthesizing hyaluronan from the cells transformed in iv);
vi) Recovery of a plasmid DNA from the cells selected in v), transformation of *Escherichia coli* cells with the plasmid DNA, and recovery of the plasmid DNA from the *E. coli* cells; and
vii) isolation of a cDNA encoding the polypeptide of the hyaluronan synthase of mouse origin by repeating three more times the above steps iv) to vi) using the recovered plasmid DNA.

(2) Cloning of a cDNA Encoding a Polypeptide of the Hyaluronan Synthase of Human Origin:
i) preparation of a probe for screening a human cDNA library based on the result of sequencing of the cDNA isolated in vii) of (1) above;
ii) screening of cDNA clones of human hyaluronan synthase using the probe prepared in i); and iii) nucleotide sequencing.

The method of producing the DNA of the present invention is not to be limited to the above method. The DNA of the present invention can be prepared by PCR method as described above or other known cDNA cloning methods.

An example of the method of producing the DNA of the present invention is described in detail below.

1. Cloning of a cDNA Encoding a Polypeptide of Hyaluronan Synthase Derived from an Organism Except Human (1) Selection of Cell Lines Capable of High Level Production of Hyaluronan and Preparation of Mutant Cells Deficient in Hyaluronan-synthesizing Ability (1-1) Selection of Cells Capable of High Level Production of Hyaluronan Cells capable of high level production of hyaluronan (hereinafter also simply referred to as "high level hyaluronan-producing cells") are selected using cells of an organism except human having the hyaluronan synthase activity. Though the cells of an organism except human having the hyaluronan synthase activity are not particularly limited, eucaryotic cells are preferable, mammalian cells are more preferable, and mouse cells are particularly preferable. Established cultured cell lines (hereinafter also simply referred to as "cell line") are preferably used in view of availability, easiness to handle, and ability to proliferate. Mouse-derived cell lines are more preferable. Among the mouse-derived cell lines, FM3A, a mouse mammary carcinoma cell line (Health Science Research Resources Bank; cell number, JCRB0701, or RIKEN Cell Bank; cell number, RCB0086) is particularly preferable. Furthermore, among FM3A, FM3A P15A that is a cell line selected taking high metastatic ability to lung as an index (Honma, Y., Kasukabe, T., and Hozumi, M. (1981) Gann 72, 898–905; Kimata, K., Honma, Y., Okayama, M., Oguri, K., Hozumi, M., and Suzuki, S. (1983) Cancer Res. 43, 1347–1354) is most preferable because of its high hyaluronan synthase activity.

Culture media used for culturing the above-described cultured cells are not particularly limited as long as cells can grow therein. Any media known in the field of cell culture can be used. For example, Eagle's minimum essential medium or the like is preferable since it has been widely used in usual culturing, readily available, and allows the above-described cells to grow. The pH of the medium is adjusted preferably to the neutral region, particularly to pH 7.0. Heat-inactivated bovine serum is preferably added to the medium to about 10%. Furthermore, amino acids and vitamins are preferably added to the medium in the order of double with respect to the usual amounts. Substances such as penicillin and streptomycin can be added to prevent proliferation of contaminating microorganisms. The above-described cells can be maintained or proliferated with the above medium in a dish or a roller bottle by the usual culturing method. The culture can be preferably performed in a carbon dioxide incubator; the concentrations of carbon dioxide and air in the incubator are preferably adjusted to 3 to 7% and 97 to 93%, respectively. The temperature is preferably adjusted to about 37 to 38° C.

The method of selecting the high level hyaluronan-producing cells is not particularly limited as long as it enables evaluation of the hyaluronan-producing ability of the cells. For example, a method utilizing fixed erythrocyte exclusion assay (Knudson, W. and Knudson, C. B. (1991) J. Cell. Sci. 99, 227–235) can be used. In the fixed erythrocyte exclusion assay, the degree of formation of extracellular hyaluronan matrix can be observed taking as an index the distance that fixed erythrocytes cannot come close to the cells. More specifically, the longer the distance that fixed erythrocytes cannot come close to the cells is, the thicker the hyaluronan matrix is formed. The hyaluronan-producing ability of the cells can be evaluated by observing the degree of formation of extracellular hyaluronan matrix using the fixed erythrocyte exclusion assay. The example as described below specifically demonstrates the fixed erythrocyte exclusion assay.

The high level hyaluronan-producing cells as selected in the above method are used in the preparation of a poly(A)$^+$ RNA.

(1-2) Preparation of Mutant Cells Deficient in the Hyaluronan-synthesizing Ability Mutant cells deficient in the hyaluronan-synthesizing ability (hereinafter also simply referred to as "cells incapable of synthesizing hyaluronan") can be obtained by mutagenizing the high level hyaluronan-producing cells as selected in (1-1) above by exposing the cells to physical or chemical stimulation to some extent that the cells do not die. The physical stimulation includes, for example, treatment with radiation such as X-ray or γ-ray. The chemical stimulation includes treatment with a mutagen such as an alkylating agent. Preferable alkylating agents include nitrosoguanidine and its derivatives, for example, N-methyl-N'-nitro-N-nitrosoguanidine or the like. When N-methyl-N'-nitro-N-nitrosoguanidine is used as a mutagen, its concentration is preferably about 0.5 μg/ml. The cells incapable of synthesizing hyaluronan can be selected and recovered from the cells mutagenized by the above method, according to a method for evaluating the hyaluronan-producing ability, such as the fixed erythrocyte exclusion assay (described in detail in the following example).

(1-3) Preparation of Cells Incapable of Synthesizing Hyaluronan Used as a Host into which a Recombinant DNA is Transfected When the cells incapable of synthesizing hyaluronan prepared in (1-2) above are used as a host into which a recombinant DNA is transfected as in (4) shown below, the cells have been preferably transformed so as to express polyoma large T antigen. For the transformation, the cells have been preferably transformed with a plasmid carrying the polyoma T antigen gene. An example of the plasmid carrying the polyoma T antigen gene is pdl3027 plasmid (Nagata, Y., Yamashiro, S. Yodoi, J., Lloyd, K. O, Shiku, H., and Furukawa, K. (1992) J. Biol. Chem. 267, 12082–12089). The thus-obtained cells incapable of synthesizing hyaluronan and expressing polyoma large T antigen (hereinafter also simply referred to as "T antigen-expressing cells incapable of synthesizing hyaluronan") can be used in (4) below as a host into which a recombinant DNA is transfected.

(2) Isolation of a Poly(A)$^+$ RNA Containing an mRNA Corresponding to the Polypeptide of Hyaluronan Synthase from the High Level Hyaluronan-producing Cells Prepared in (1-1) Above (2-1) Preparation of the Total RNA The total RNA can be obtained by the known method (Kingston, R. E. (1991) Current Protocols in Molecular Biology, Suppl. 14, Unit 4.2, Greene Publishing Associates and Wiley Interscience, New York, etc.). Although a total RNA can be obtained from the high level hyaluronan-producing cells prepared in (1-1) above by the method usually used for preparing a total RNA, a preferable method includes the guanidine thiocyanate/CsCl method (Kingston, R. E. (1991) Current Protocols in Molecular Biology, Suppl. 14, Unit 4.2, Greene Publishing Associates and Wiley Interscience, New York).

(2-2) Preparation of a Poly(A)$^+$ RNA

A poly(A)$^+$ RNA can be purified from the total RNA obtained in (2-1) above by oligo-(dT) cellulose column chromatography or the like.

(3) Preparation of a cDNA Library (3-1) Synthesis of cDNA cDNA can be synthesized by the reverse transcriptase reaction using the poly(A)$^-$ RNA prepared in (2) above as a template. Specifically, the methods usually used in the field of gene engineering may be used. Alternatively, a commercially available cDNA synthesizing kit may be used. Though oligo(dT), which is usually used as a primer, can be used as a primer in the reverse transcriptase reaction, a random oligo nucleotide primer is preferably used.

(3-2) Preparation of a cDNA Library

A cDNA library can be obtained by ligating the cDNA obtained in (3-1) above to a cloning vector.

Although the cloning vector to which the cDNA is ligated is not particularly limited, an expression vector functioning in mammalian cells is preferably used. In order to make the subsequent procedure readily operable, it is preferable to use a shuttle vector having a replication origin functioning in cells such as *Escherichia coli* (*E. coli*). A preferable vector may be pcDNAI (manufactured by Invitrogen Co.). The cDNA obtained in (3-1) above is ligated to the above-described cloning vector to give a recombinant DNA (cDNA library).

(4) Transfection of the Recombinant DNA Prepared in (3) Above into the Cells Incapable of Synthesizing Hyaluronan The recombinant DNA (cDNA library) obtained by ligating the cDNA to the cloning vector is transfected into host cells. The host cells to be used should be selected depending on the cloning vector used. For example, when an expression vector functioning in mammalian cells is used as a cloning vector, host cells should be mammalian cells. Alternatively, the cDNA library may be prepared by selecting host cells first and then selecting a cloning vector suitable for the host cells.

When cloning is performed using the presence of hyaluronan-synthesizing ability as an index, it is preferable to use as host cells the cells incapable of synthesizing hyaluronan as prepared in (1) above. The T antigen-expressing cells incapable of synthesizing hyaluronan prepared in (1-3) above are most preferably used.

The DNA can be transfected into the host cells by the method usually used in the field of gene engineering. A commercially available reagent for transformation can also be used. As such a reagent, Lipofectoamine™ reagent (Life Technologies, Inc) is suitably used. The transformed T antigen-expressing cells incapable of synthesizing hyaluronan are cultured using the medium and the method as described in (1-1) above. Though the culturing period is not particularly limited, about 64 hours are preferable.

(5) Selection of Cells Capable of Synthesizing Hyaluronan from Transformants Obtained in (4) Above (5-1) Preparation of Labeled Hyaluronan-binding Protein Used for Detecting Hyaluronan Among the host cells into which the cDNA library has been transfected, the T antigen-expressing cells incapable of synthesizing hyaluronan, into which the recombinant DNA containing the cDNA encoding the polypeptide of hyaluronan synthase has been transfected, express the polypeptide of hyaluronan synthase by culturing the cells by the method as described in (4) above so that hyaluronan can be synthesized and accumulated extracellularly. The T antigen-expressing cells incapable of synthesizing hyaluronan, into which the recombinant DNA containing cDNA encoding the polypeptide of hyaluronan synthase has been transfected, can be selected by detecting cells in which hyaluronan is accumulated extracellularly. Though the method of detecting extracellularly accumulated hyaluronan is not particularly limited, the detection is preferably performed by using a protein capable of binding to hyaluronan (herein also referred to as "hyaluronan-binding protein") that is labeled (herein also referred to as "labeled hyaluronan-binding protein"). The hyaluronan-binding protein is not particularly limited. Examples thereof include aggrecan, neurocan, versican, link protein, hyaluronectin, hyaluronan-binding protein derived from human synovial fluid, brain hyaluronan-binding protein, and CD44. Among these, aggrecan is preferably used. Particularly, the hyaluronan-binding region of aggrecan (herein also abbreviated as "HABR") is preferably used.

A substance used to label the hyaluronan-binding protein is not particularly limited. Examples thereof include biotin, avidin (including streptoavidin), fluorescent substances, enzymes, and radioisotopes. Biotin is preferably used. The method of labeling the hyaluronan-binding protein using the above labels is not particularly limited. A known labeling method can be used.

When biotin is used to label the hyaluronan-binding protein, for example, avidin labeled with a fluorescent substance is used to detect the biotin. A commercially available labeled avidin can also be used. Further, biotinated HABR, which is an example of the labeled hyaluronan-binding protein, will be described in the following example for its specific preparation method.

(5-2) Selection of Cells Capable of Synthesizing Hyaluronan

The T antigen-expressing cells incapable of synthesizing hyaluronan transformed in (4) above are contacted with the labeled hyaluronan-binding protein obtained in (5-1) above and the mixture is incubated. The cells capable of synthesizing hyaluronan can be selected by detecting and selecting cells in which hyaluronan is accumulated extracellularly. Further, when the hyaluronan-binding protein is labeled with biotin, the cells need to be incubated with labeled avidin to contact together after incubation with the biotin-labeled hyaluronan-binding protein. The cells are preferably washed after every incubation. The incubation conditions are not particularly limited as long as binding of hyaluronan to the hyaluronan-binding protein is not inhibited. Preferably, the incubation is performed at a neutral pH and on ice (0° C.). Though the incubation period is not also particularly limited, it is preferably about 1 hour.

After the incubation, a known detection method for the label is suitably selected depending upon the type of the label used, thereby detecting cells (positively stained cells) on which the label is found extracellularly (on the cell surface). Thus, the cells capable of synthesizing hyaluronan can be selected. When a fluorescent substance is used as a label, detection of the label and selection of the cells can be concurrently done by means of flow cytometry.

(6) Recovery of a Plasmid DNA from the Cells Selected in (5) Above, Transformation of E. coli with the Recovered Plasmid DNA, and Recovery of the Plasmid DNA from the Transformed E. coli A plasmid DNA (a recombinant DNA) is recovered from the cells capable of synthesizing hyaluronan selected in (5) above and the resulting recombinant DNA is used to transform Escherichia coli (E. coli). The method of recovering plasmid DNA is performed with the commonly used technique in the field of gene engineering. It is not particularly limited thereto, but the method of Hirt (Hirt, B. (1967) J. Mol. Biol. 26, 365–369) is preferably used.

E. coli is transformed with the recovered DNA and cultured by the usual method for culturing E. coli. The plasmid DNA (recombinant DNA) is then recovered from the resulting E. coli.

(7) Isolation of the cDNA

As described above, the cDNA encoding the polypeptide of hyaluronan synthase can be isolated. In order to confirm that the cDNA obtained actually encodes the polypeptide of hyaluronan synthase, the above steps (4) to (6) are preferably repeated about three more times.

The cDNA thus obtained is subjected to sequencing as it is or after subcloned into an appropriate plasmid. 2. Cloning of the cDNA encoding the polypeptide of human hyaluronan synthase (1) Preparation of Probes for Screening of the cDNA Library The nucleotide sequence of the cDNA corresponding to the polypeptide of hyaluronan synthase derived from an organism except human determined as described above is compared with that of the cDNA of hyaluronan synthase derived from a microorganism, preferably Streptococcus to determine the regions that are conserved (herein also simply referred to as "conserved regions"), which can be used as a 5' primer and a 3' primer in polymerase chain reaction (PCR). Thereafter, each conserved region is synthesized.

Labeled DNA probes used for screening the cDNA library can be prepared by the DNA labeling method usually used in the field of gene engineering using the primers prepared based on the conserved regions (the 5' primer and the 3' primer) from the hyaluronan synthase gene derived from an organism except human as obtained in the item 1 above. In present invention, a radioisotope and a fluorescent substance can be used as a label. A fluorescent substance is preferably used. The labeled DNA probe can be efficiently prepared in a large quantity by PCR.

(2) Screening of Clones of cDNA of Human Hyaluronan Synthase Using the Probes Prepared in (1) Above (2-1) Preparation of a cDNA Library A total RNA is prepared from cells derived from human and a poly(A)$^+$ RNA is prepared from the total RNA. A cDNA can be synthesized by the reverse transcriptase reaction using the poly(A)$^+$ RNA as a template. These procedures are all performed by the methods usually used in the field of gene engineering. Specifically, the methods as described in (2) and (3) in item 1 above may be used.

The cDNA is ligated to a cloning vector. Though the cloning vector is not particularly limited, for example, λgt11 digested with EcoRI is preferably used. Alternatively, a commercially available human cDNA-ligated cloning vector may be used.

During the process for achieving the present invention, cDNA clones of human hyaluronan synthase were selected, as demonstrated in the example, from a human cDNA library using probes prepared based on the mouse cDNA sequence. The cDNA can be ligated to an expression vector functioning in mammalian cells and selected using the expression product as an index.

(2-2) Screening of the cDNA Clones of Human Hyaluronan Synthase

From the cDNA library obtained as described above, phage clones having the full-length of the cDNA of hyaluronan synthase can be selected by hybridization using the probe prepared in (1) above. The hybridization can be performed by the method usually used in the field of gene engineering, for example, plaque hybridization or the like. Plaques that hybridize with the probe can be isolated and identified by detecting the label bound to the probe. One of ordinary skill in the art can appropriately detect the label depending on the label used.

(3) Sequencing

A phage DNA is prepared from positive λgt11 clones selected in (2) above and digested with an appropriate restriction enzyme to cleave out the cDNA of hyaluronan synthase. The enzyme used for cloning the cDNA is used as the restriction enzyme. For example, when λgt11 digested with EcoRI is used as the vector, EcoRI is preferably used. The thus-obtained cDNA is subjected to sequencing as it is or after subcloned into an appropriate plasmid. When the cDNA is subcloned, pcDNA3 plasmid vector (manufactured by Invitrogen Co.) is preferably used.

The DNA as obtained above may have a substitution, deletion, or insertion of nucleotide(s) or the combination thereof, which result in substitution, deletion, or insertion of one or two or more amino acid residues of the polypeptide of hyaluronan synthase encoded by the DNA as long as the hyaluronan-synthesizing activity of the polypeptide is not substantially lowered. The substitution, deletion, or insertion of the nucleotides can be introduced in the DNA sequence by synthesizing a sequence having restriction enzyme cleavage sites at the both ends and containing the both sides of the mutated site and replacing it with the corresponding non-mutated DNA sequence. The site-directed mutation method (Kramer, W. and Frits, H. J. (1987) Meth. in Enzymol. 154, 350; Kunkel, T. A. et al. (1987) Meth. in Enzymol. 154, 367) or the like can also be used for introducing the substitution, deletion, or insertion, or the combination thereof into the DNA sequence.

The method of measuring the hyaluronan-synthesizing activity is well known in the art. Thus, one of ordinary skill in the art would readily determine the substitution, deletion, or insertion, or the combination thereof that does not substantially lower the hyaluronan-synthesizing activity.

II. THE POLYPEPTIDE OF THE PRESENT INVENTION

The polypeptide of the present invention is a polypeptide of the hyaluronan synthase of human origin or a part thereof, which is encoded by the DNA of the present invention. It is preferably a polypeptide of the hyaluronan synthase having the amino acid sequence (amino acid numbers 1 to 543) shown by SEQ ID NO: 4.

Since the amino acid sequence is revealed by the present invention, the polypeptide of the present invention can be synthesized based on the amino acid sequence. It is possible and preferable, however, to obtain the polypeptide by expressing the DNA of the present invention.

For example, the DNA of the present invention is ligated to an appropriate expression vector functioning in mammalian cells and cells carrying this vector are cultured in an appropriate medium to produce and accumulate the polypeptide of hyaluronan synthase in the culture (in the cells and/or the medium). The polypeptide of hyaluronan synthase is then extracted from the culture. In this way, the polypeptide of hyaluronan synthase can be produced. In this procedure, the usually used methods for extracting and purifying enzymes can be used.

Specifically, examples of the extraction method include cell disruption due to, for example, ultrasonication, homogenization, osmotic shock procedure, freezing and thawing method, treatment with a surfactant, and the combined process thereof. Further, specific examples of the purification methods include salting out with ammonium sulfate or sodium sulfate, centrifugation, dialysis, ultrafiltration, adsorption chromatography, ion exchange chromatography, hydrophobic chromatography, reverse phase chromatography, gel filtration, gel permeation chromatography, affinity chromatography, electrophoresis, and the combined process thereof.

The DNA of the present invention can be expressed using a host-vector system usually used for producing proteins. The host-vector system is preferably an animal cell system, particularly, a mammalian cell system. The DNA of the present invention may be expressed alone or as a fusion protein together with another protein. The full-length of the DNA may be expressed. Alternatively, part of the DNA may be expressed to produce a partial peptide.

The polypeptide of hyaluronan synthase as produced above or its partial peptide, or a fusion protein thereof with another protein can be used to produce antibodies that bind to the hyaluronan synthase. The antibodies can be prepared by the usual methods for producing antibodies. Monoclonal antibodies that bind to the hyaluronan synthase can also be produced by the usual methods.

BEST MODE OF CARRYING OUT THE INVENTION

The present invention will be described in more detail with reference to the following example.

First, the methods commonly used throughout the example are described.

1. Fixed Erythrocyte Exclusion Assay

Cells were inoculated on a 35-mm tissue culture dish and cultured at 37° C. for 3 days. The culture medium was replaced with 750 μl of a suspension of fixed sheep erythrocytes (manufactured by Inter-Cell Technologies, Inc.) ($10^8$ cells/ml). After the dish was allowed to stand for 10 minutes, extracellular hyaluronan matrix were observed as the region that the erythrocytes could not come close to. The observation was performed using a phase-contrast microscope (OLYMPUS IMT-2; manufactured by Olympus Optical Co.) with 200-fold magnification.

2. Preparation of Biotinated Hyaluronan-binding Region (b-HABR)

Aggrecan was extracted from bovine nasal cartilage with a guanidine solution and purified by cesium chloride density gradient centrifugation under association and dissociation conditions. The hyaluronan-binding region of the purified aggrecan (2 mg) was protected by hyaluronan and the protected aggrecan was reacted with 0.57 mg of NHS-LC-biotin (manufactured by Pierce) at room temperature for 2 hours for biotination. The biotinated aggrecan was partially digested with trypsin and the digested product was subjected to gel filtration using a Sephacryl S-300 column (manufactured by Pharmacia) and then hyaluronan affinity chromatography (Tengblad, A. (1979) Biochem. Biophys. Acta 578, 281–289). Thus, b-HABR was purified.

A production example of the DNA of the present invention is described below.

1. Cloning of a cDNA Encoding a Polypeptide of a Hyaluronan Synthase of Mouse Origin (1) Selection of High Level Hyaluronan-producing Cells and Preparation of Cells Incapable of Synthesizing Hyaluronan (1-1) Selection of High Level Hyaluronan-producing Cells FM3A P-15A having high metastatic ability to lung was selected and established as a cell line derived from mouse mammary carcinoma cell line FM3A (Health Science Research Resources Bank; cell number, JCRB0701), which is one of mouse-derived established cell lines. FM3A P-15A cells were cultured in Eagle's minimum essential medium (manufactured by Nissui Pharmaceutical) containing 10% heat-inactivated bovine serum, doubled concentrations of amino acids and vitamins, penicillin, and streptomycin in a 100-mm petri dish (manufactured by Falcon. No. 1005). Culture was performed under the condition of 37° C. in 5% $CO_2$.

The degree of formation of extracellular hyaluronan matrix in the FM3A P-15A culture was examined by the fixed erythrocyte exclusion assay. Cells that extracellularly formed hyaluronan matrix in a larger amount compared with the other cells were collected and pooled. The resulting cells (high level hyaluronan-producing cells) were designated as FM3A HA1.

(1-2) Preparation of Cells Incapable of Synthesizing Hyaluronan

The high level hyaluronan-producing cells selected in (1-1) above were treated with 0.5 μg/ml of N-methyl-N'-nitro-N-nitrosoguanidine (manufactured by Nacalai Tesque Co.) and examined for the degree of formation of extracellular hyaluronan matrix by fixed erythrocyte exclusion assay. Cells that did not extracellularly form hyaluronan matrix were collected and pooled. The thus-obtained cells incapable of synthesizing hyaluronan were designated as $HAS^-$ cells.

(1-3) Preparation of $HAS^-$ Cells that Express Polyoma Large T Antigen

Plasmid pdl3027 containing the polyoma T antigen gene (given by Dr. K. Furukawa (Nagasaki University) and Dr. C. Basilico (New York University)) and plasmid pSV2neo (manufactured by CLONTECH Co.) were transfected into $HAS^-$ cells as obtained above. The cells were selected through treatment with 500 μg/ml G-418 (manufactured by Gibco Co.). Thus, $HAS^-$ cells that constantly express polyoma large T antigen (herein also referred to as "HAS-P cells") were prepared.

(2) Isolation of a Poly(A)$^+$ RNA from FM3A HA1

(2-1) Preparation of a Total RNA

A total RNA was prepared from FM3A HA1 by the guanidine thiocyanate/CsCl method (Kingston, R. E. (1991) Current Protocols in Molecular Biology, Suppl. 14, Unit 4.2, Greene Publishing Associates and Wiley Interscience, New York).

(2-2) Preparation of a Poly(A)$^+$ RNA

A poly(A)$^+$ RNA was purified from the total RNA obtained in (2-1) above by oligo-(dT) cellulose column chromatography.

(3) Preparation of a cDNA Library (3-1) Synthesis of cDNA cDNA was synthesized by reverse transcriptase reaction using the poly(A)$^-$ RNA obtained in (2-2) above as a template, and random oligonucleotide primers as primers.

(3-2) Preparation of a cDNA Library

The cDNA obtained in (3-1) above was ligated to pcDNAI (manufactured by Invitrogen Co.), an expression vector functioning in mammalian cells, to prepare a cDNA library.

(4) Transformation by the cDNA Library

The cDNA library prepared in (3-2) above was transfected into HAS-P cells prepared in (1-3) above using Lipofectoamine™ reagent, manufactured by Life Technologies, Inc. The transformed HAS-P cells were cultured in the medium under the conditions as described in (1-1) above for 64 hours.

(5) Selection of Cells Capable of Synthesizing Hyaluronan from Transformants

After 64-hour culturing as described in (4) above, the transformants were washed with a cooled medium (Cosmedium001 (manufactured by Cosmo Bio)) and then suspended in the same medium but containing 50 μg/ml of b-HABR. After 1 hour, the cells were washed with cooled Cosmedium001 and suspended in the same medium but containing avidin labeled with fluorescein (fluorescein avidin DCS, manufactured by Vector Laboratories, Inc.). After 1 hour, the cells were washed with cooled phosphate-buffered saline (PBS) containing 5% fetal calf serum and suspended in the same solution. Positively stained cells were selected using a flow cytometer (EPICS Elite Flow Cytometer, manufactured by Coulter Electronics, Inc.).

(6) Recovery of a Plasmid DNA from the Cells Selected in (5) Above, Transformation of E. coli with the Recovered Plasmid DNA, and Recovery of the Plasmid DNA from E. coli Transformants A plasmid DNA was recovered from the cells selected in (5) above by the method of Hirt (Hirt, B. (1967) J. Mol. Biol. 26, 365–369). Specifically, this procedure was performed in the following manner. The cells selected in (5) above were dissolved in 100 μl of 0.6% sodium dodecyl sulfate (SDS)/10 mM ethylenediamine-tetraacetic acid (EDTA) solution and the mixture was allowed to stand at the room temperature for 20 minutes. Twenty-five ml of 5M NaCl was then added thereto and the mixture was allowed to stand overnight on ice. The solution was treated with phenol and chloroform and then precipitated with ethanol to recover a plasmid DNA. The recovered plasmid DNA was used to transform E. coli MC1061/P3 (manufactured by Invitrogen Co.) by electroporation. The resulting transformants were cultured and the plasmid DNA was then recovered therefrom.

(7) Isolation of the cDNA Encoding the Polypeptide of Hyaluronan Synthase

The above steps (4) to (6) (steps of transformation and selection) were repeated three more times using the plasmid DNA recovered from the transformed E. coli MC1061/P3 obtained in (6) above to isolate cDNA encoding the polypeptide of hyaluronan synthase. The thus-isolated cDNA encoding the polypeptide of hyaluronan synthase was designated as pcDNAI-HAS.

(8) Determination and Analysis of the cDNA Sequence Encoding the Polypeptide of Hyaluronan Synthase The cDNA clone isolated in (7) above was subcloned into a plasmid vector, pcDNA3 (manufactured by Invitrogen Co.). The thus-obtained recombinant plasmid was designated as pcDNA3-HAS. pcDNA3-HAS was denatured with alkali and its nucleotide sequence of both sense and anti-sense directions was determined using [$^{35}$S]dCTP and dea-zaGTP kit (manufactured by U.S. Biochemical Co.) and DNA polymerase (Sequenase ver 2.0, manufactured by U.S. Biochemical Co.).

DNA synthesis for sequencing was performed using primers synthesized based on T7, SP6, and the nucleotide sequence existing at about 250 bp intervals in pcDNA3. The thus-obtained DNA sequence was analyzed by GENETYX-MAC computer program (manufactured by Software Development Co.). The nucleotide sequence and the deduced amino acid sequence therefrom were analyzed utilizing a database for analyzing nucleic acids and proteins (EMBL-GDB, Release44, and NBRF-PDB, Release 45). The amino acid sequence of the polypeptide of hyaluronan synthase originating from Streptococcus (Streptococcus pyogenes) was compared with that of the polypeptide of the hyaluronan synthase originating from mouse. Two regions that conserved in both of the polypeptides of hyaluronan synthase were found and designated as HAS-1 and HAS-2, respectively. The nucleotide sequences corresponding to these regions are shown by SEQ ID NO: 2 (HAS-1) and SEQ ID NO: 3 (HAS-2).

2. Production of the DNA of the Present Invention

(1) Preparation of Probes for Screening a Human cDNA Library

An oligonucleotide having the sequence of HAS-1 and that having the sequence of HAS-2 were synthesized.

Fluorescence-labeled DNA probes used for screening the cDNA library were prepared from the mouse-origin hyaluronan synthase gene obtained in the item 1 above by PCR method with ECL™ probe-amp reagents (manufactured by Amersham Co.) using primers produced based on the conserved regions (HAS-1 and HAS-2; using as a 5' primer an oligonucleotide having the sequence of HAS-1 and as a 3' primer an oligonucleotide having the sequence of HAS-2). PCR amplification was performed 30 cycles using Gene-Amp PCR reagent kit (manufactured by Takara Shuzo) (Each cycle consisted of denaturation at 95° C. for 1 minute, annealing at 50° C. for 2 minutes, and extension at 72° C. for 3 minutes.). The PCR products were analyzed by 2% agarose gel electrophoresis.

(2) Screening of the cDNA Clones of Human Hyaluronan Synthase Using the Probes Prepared in (1)

For isolating a human homolog of the hyaluronan synthase gene, human fetal brain cDNA library constructed in λgt11 (manufactured by CLONTECH) was mixed with indicator bacteria and melted soft agar. The mixture was layered on an agar plate and cultured. As a result, $1 \times 10^6$ plaques were formed.

The plaques derived from the λgt11 cDNA library as obtained above were screened. The plaques were transferred onto a commercially available nylon membrane (Hybond N+ ™ nylon membrane, manufactured by Amersham) and the phage DNA was fixed on the nylon membrane by the alkaline fixation method recommended in the instructions appended to the product.

This filter was allowed to hybridize with the probes prepared in (1) above in 5×SSC containing 0.1% SDS, 5% (w/v) dextran sulfate, and 100 μg/ml denatured salmon sperm DNA at 60° C. for 12 hours. The filter was washed with 1×SSC containing 0.1% SDS at 60° C. for 15 minutes, then 0.5×SSC containing 0.1% SDS at 60° C. for 15 minutes. Positive clones were detected with ECL™ detection kit (manufactured by Amersham).

(3) Sequencing

The recombinant vector was purified from the λgt11 positive clones and digested with EcoRI to excise the cDNA insert as a single fragment. This fragment was subcloned into a plasmid vector, pcDNA3 (manufactured by Invitrogen Co.). The nucleotide sequence of the isolated cDNA was determined by repeatedly sequencing both strands of the alkali-denatured plasmid DNA using [$^{35}$S]dGTP and deaza-GTP kit and DNA polymerase (Sequenase version 2.0, manufactured by U.S. Biochemical Co.). DNA synthesis for sequencing was started with primers synthesized based on T7, SP6, and the nucleotide sequence existing at about 250 intervals in pcDNA3. The DNA sequences obtained were compiled and analyzed using GENETYX-MAC computer program (manufactured by Software Development Co.). The nucleotide sequence and the deduced amino acid sequence therefrom were analyzed using a database for analyzing nucleic acids and proteins (EMBL-GDB, Release44, and NBRF-PDB, Release45). The determined nucleotide sequence is shown by SEQ ID NO: 1. The amino acid sequence encoded by the open reading frame existing in this nucleotide sequence (from position 149 to position 1777) is shown by SEQ ID NO: 4.

INDUSTRIAL APPLICABILITY

The polypeptide of the present invention can be used for mass production of hyaluronan, which is used as an ingredient of medicines and cosmetics at present, in an industrial scale, and for medicines for diseases caused by decreased expression of hyaluronan. The polypeptide of the present invention can also be used for development of hyaluronan synthase-specific inhibitors. Furthermore, the polypeptide can be used as an antigen to produce antibodies specific to the hyaluronan synthase. The DNA of the present invention can be used for mass production of the polypeptide of hyaluronan synthase in an industrial scale, and for gene therapy for diseases caused by decreased expression of hyaluronan. Moreover, an antisense DNA and an antisense RNA of the DNA of present invention can be used for gene therapy for metastasis inhibitors.

The DNA of the present invention can also be used as a reagent for research purpose.

What is claimed is:

1. An isolated DNA encoding a human origin polypeptide which comprises at least a fragment of the amino acid sequence set forth in SEQ ID NO:4 and which has hyaluronan synthase activity.

2. The isolated DNA according to claim 1, which encodes the polypeptide of SEQ ID NO:4.

3. The isolated DNA according to claim 1, which comprises at least a fragment of the nucleic acid sequence set forth in SEQ ID NO:1.

4. The isolated DNA according to claim 3, which comprises the nucleic acid sequence from position 149 to position 1777 set forth in SEQ ID NO:1.

5. An isolated DNA hybridizable with a nucleic acid complementary to the nucleic acid sequence set forth in SEQ ID NO: 1 in 5×SSC containing 0.1% SDS, 5%(w/v) dextran sulfate, and 100 µg/ml denatured salmon sperm DNA at 60° C. for 12 hours, wherein said DNA encodes a polypeptide that has hyaluronan synthase activity.

6. The isolated DNA according to claim 5, wherein the hybrid of the isolated DNA and the nucleic acid complementary to the nucleic acid sequence set forth in SEQ ID NO: 1 is stable after washing with 1×SSC containing 0.1% SDS at 60° C. for 15 minutes, and then with 0.5×SSC containing 0.1% SDS at 60° C. for 15 minutes.

* * * * *

SEQUENCE LISTING

```
<160> NUMBER OF SEQ ID NOS: 4

<210> SEQ ID NO 1
<211> LENGTH: 2117
<212> TYPE: DNA
<213> ORGANISM: HUMAN
<220> FEATURE:
<221> NAME/KEY: CDS
<222> LOCATION: (149)...(1777)

<400> SEQUENCE: 1
gaattccggg cgcccgggac tcacgcccct tcctttcccc tctcgctccc agcaggacgc      60
gcccaagccc actcctgcag cccgccgctg ctccggcctg gcccggaggg tgctgaccat     120
cgccttcgcc ctgctcatcc tggccctc atg acc tgg gcc tac gcc gcc ggg       172
                                Met Thr Trp Ala Tyr Ala Ala Gly
                                  1               5 gtg ccg ctg gcc tcc gat cgc tac ggc ctc ctg gcc ttc ggc ctc tac      220
Val Pro Leu Ala Ser Asp Arg Tyr Gly Leu Leu Ala Phe Gly Leu Tyr
```

-continued

```
             10                    15                    20
ggg gcc ttc ctt tca gcg cac ctg gtg gcg cag agc ctc ttc gcg tac        268
Gly Ala Phe Leu Ser Ala His Leu Val Ala Gln Ser Leu Phe Ala Tyr
 25                  30                  35                  40 ctg gag cac cgg cgg gtg gcg gcg gcg gcg cgg ggg ccg ctg gat gca        316
Leu Glu His Arg Arg Val Ala Ala Ala Ala Arg Gly Pro Leu Asp Ala
                 45                  50                  55 gcc acc gcg cgc agt gtg gcg ctg acc atc tcc gcc tac cag gag gac        364
Ala Thr Ala Arg Ser Val Ala Leu Thr Ile Ser Ala Tyr Gln Glu Asp
                     60                  65                  70 ccc gcg tac ctg cgc cag tgc ctg gcg tcc gcc cgc gcc ctg ctg tac        412
Pro Ala Tyr Leu Arg Gln Cys Leu Ala Ser Ala Arg Ala Leu Leu Tyr
         75                  80                  85 ccg cgc gcg cgc gtg cgc gtc ctc atg gtg gtg gat ggc aac cgc gcc        460
Pro Arg Ala Arg Val Arg Val Leu Met Val Val Asp Gly Asn Arg Ala
         90                  95                 100 gag gac ctc tac atg gtc gac atg ttc cgc gag gtc ttc gct gac gag        508
Glu Asp Leu Tyr Met Val Asp Met Phe Arg Glu Val Phe Ala Asp Glu
105                 110                 115                 120 gac ccc gcc acg tac gtg tgg gac ggc aac tac cac cag ccc tgg gaa        556
Asp Pro Ala Thr Tyr Val Trp Asp Gly Asn Tyr His Gln Pro Trp Glu
                    125                 130                 135 ccc gcg gcg gcg ggc gcg gtg ggc gcc gga gcc tat cgg gag gtg gag        604
Pro Ala Ala Ala Gly Ala Val Gly Ala Gly Ala Tyr Arg Glu Val Glu
                140                 145                 150 gcg gag gat cct ggg cgg ctg gca gtg gag gcg ctg gtg agg act cgc        652
Ala Glu Asp Pro Gly Arg Leu Ala Val Glu Ala Leu Val Arg Thr Arg
            155                 160                 165 agg tgc gtg tgc gtg gcg cag cgc tgg ggc ggc aag cgc gag gtc atg        700
Arg Cys Val Cys Val Ala Gln Arg Trp Gly Gly Lys Arg Glu Val Met
170                 175                 180 tac aca gcc ttc aag gcg ctc gga gat tcg gtg gac tac gtg cag gtc        748
Tyr Thr Ala Phe Lys Ala Leu Gly Asp Ser Val Asp Tyr Val Gln Val
185                 190                 195                 200 tgt gac tcg gac aca agg ttg gac ccc atg gca ctg ctg gag ctc gtg        796
Cys Asp Ser Asp Thr Arg Leu Asp Pro Met Ala Leu Leu Glu Leu Val
                    205                 210                 215 cgg gta ctg gac gag gac ccc cgg gta ggg gct gtt ggt ggg gat gtg        844
Arg Val Leu Asp Glu Asp Pro Arg Val Gly Ala Val Gly Gly Asp Val
                220                 225                 230 cgg atc ctt aac cct ctg gac tcc tgg gtc agc ttc cta agc agc ctg        892
Arg Ile Leu Asn Pro Leu Asp Ser Trp Val Ser Phe Leu Ser Ser Leu
            235                 240                 245 cga tac tgg gta gcc ttc aat gtg gag cgg gct tgt cag agc tac ttc        940
Arg Tyr Trp Val Ala Phe Asn Val Glu Arg Ala Cys Gln Ser Tyr Phe
        250                 255                 260 cac tgt gta tcc tgc atc agc ggt cct cta ggc cta tat agg aat aac        988
His Cys Val Ser Cys Ile Ser Gly Pro Leu Gly Leu Tyr Arg Asn Asn
265                 270                 275                 280 ctc ttg cag cag ttt ctt gag gcc tgg tac aac cag aag ttc ctg ggt       1036
Leu Leu Gln Gln Phe Leu Glu Ala Trp Tyr Asn Gln Lys Phe Leu Gly
                285                 290                 295 acc cac tgt act ttt ggg gat gac cgg cac ctc acc aac cgc atg ctc       1084
Thr His Cys Thr Phe Gly Asp Asp Arg His Leu Thr Asn Arg Met Leu
                300                 305                 310 agc atg ggt tat gct acc aag tac acc tcc agg tcc cgc tgc tac tca       1132
Ser Met Gly Tyr Ala Thr Lys Tyr Thr Ser Arg Ser Arg Cys Tyr Ser
            315                 320                 325 gag acg ccc tcg tcc ttc ctg cgg tgg ctg agc cag cag aca cgc tgg       1180
```

```
Glu Thr Pro Ser Ser Phe Leu Arg Trp Leu Ser Gln Gln Thr Arg Trp
    330                 335                 340 tcc aag tcg tac ttc cgt gag tgg ctg tac aac gcg ctc tgg tgg cac       1228
Ser Lys Ser Tyr Phe Arg Glu Trp Leu Tyr Asn Ala Leu Trp Trp His
345                 350                 355                 360 cgg cac cat gcg tgg atg acc tac gag gcg gtc gtc tcc ggc ctg ttc       1276
Arg His His Ala Trp Met Thr Tyr Glu Ala Val Val Ser Gly Leu Phe
                365                 370                 375 ccc ttc ttc gtg gcg gcc act gtg ctg cgt ctg ttc tac gcg ggc cgc       1324
Pro Phe Phe Val Ala Ala Thr Val Leu Arg Leu Phe Tyr Ala Gly Arg
            380                 385                 390 cct tgg gcg ctg ctg tgg gtg ctg ctg tgc gtg cag ggc gtg gca ctg       1372
Pro Trp Ala Leu Leu Trp Val Leu Leu Cys Val Gln Gly Val Ala Leu
                395                 400                 405 gcc aag gcg gcc ttc gcg gcc tgg ctg cgg ggc tgc ctg cgc atg gtg       1420
Ala Lys Ala Ala Phe Ala Ala Trp Leu Arg Gly Cys Leu Arg Met Val
        410                 415                 420 ctt ctg tcg ctc tac gcg ccc ctc tac atg tgt ggc ctc ctg cct gcc       1468
Leu Leu Ser Leu Tyr Ala Pro Leu Tyr Met Cys Gly Leu Leu Pro Ala
425                 430                 435                 440 aag ttc ctg gcg cta gtc acc atg aac cag agt ggc tgg ggc acc tcg       1516
Lys Phe Leu Ala Leu Val Thr Met Asn Gln Ser Gly Trp Gly Thr Ser
                445                 450                 455 ggc cgg cgg aag ctg gcc gct aac tac gtc cct ctg ctg ccc ctg gcg       1564
Gly Arg Arg Lys Leu Ala Ala Asn Tyr Val Pro Leu Leu Pro Leu Ala
            460                 465                 470 ctc tgg gcg ctg ctg ctg ctt ggg ggc ctg gtc cgc agc gta gca cac       1612
Leu Trp Ala Leu Leu Leu Leu Gly Gly Leu Val Arg Ser Val Ala His
                475                 480                 485 gag gcc agg gcc gac tgg agc ggc cct tcc cgc gca gcc gag gcc tac       1660
Glu Ala Arg Ala Asp Trp Ser Gly Pro Ser Arg Ala Ala Glu Ala Tyr
        490                 495                 500 cac ttg gcc gcg ggg gcc ggc gcc tac gtg ggc tac tgg gtg gcc atg       1708
His Leu Ala Ala Gly Ala Gly Ala Tyr Val Gly Tyr Trp Val Ala Met
505                 510                 515                 520 ttg acg ctg tac tgg gtg ggc gtg cgg agg ctt tgc cgg cgg cgg acc       1756
Leu Thr Leu Tyr Trp Val Gly Val Arg Arg Leu Cys Arg Arg Arg Thr
                525                 530                 535 ggg ggc tac cgc gtc cag gtg tgagtccagc cacgcggatg ccgcctcaag          1807
Gly Gly Tyr Arg Val Gln Val
                540 ggtcttcagg ggaggccaga ggagagctgc tgggccccga gccacgaact tgctgggtgg     1867 ttctctgggc ctcagtttcc ctcctctgcc aaacgagggg gtcagcccaa gattcttcag     1927 tctggactat attgggactg ggacttctgg gtctccaggg agggtattta ttggtcagga     1987 tgtgggattt gaggagtgga ggggaagggg tcctgctttc tcctcgttct tatttaatct     2047 ccatttctac tgtgtgatca ggatgtaata aagaatttta tttattttca aaaaaaaaa     2107 accggaattc                                                            2117

<210> SEQ ID NO 2
<211> LENGTH: 32
<212> TYPE: DNA
<213> ORGANISM: Artificial Sequence
<220> FEATURE:
<223> OTHER INFORMATION: HAS-1, a region of the hyaluronan synthase gene
      which is conserved between S. pyogenes and mouse.

<400> SEQUENCE: 2
tggggcggca aacgtgaggt catgtacaca gc                                       32
```

```
<210> SEQ ID NO 3
<211> LENGTH: 35
<212> TYPE: DNA
<213> ORGANISM: Artificial Sequence
<220> FEATURE:
<223> OTHER INFORMATION: HAS-2, a region of the hyaluronan synthase gene
      which is conserved between S. pyogenes and mouse.

<400> SEQUENCE: 3
caccacagag cattgtatag ccactctcgg aagta                                35

<210> SEQ ID NO 4
<211> LENGTH: 543
<212> TYPE: PRT
<213> ORGANISM: HUMAN

<400> SEQUENCE: 4
```

Met Thr Trp Ala Tyr Ala Ala Gly Val Pro Leu Ala Ser Asp Arg Tyr
 1               5                  10                  15

Gly Leu Leu Ala Phe Gly Leu Tyr Gly Ala Phe Leu Ser Ala His Leu
            20                  25                  30

Val Ala Gln Ser Leu Phe Ala Tyr Leu Glu His Arg Arg Val Ala Ala
        35                  40                  45

Ala Ala Arg Gly Pro Leu Asp Ala Ala Thr Ala Arg Ser Val Ala Leu
    50                  55                  60

Thr Ile Ser Ala Tyr Gln Glu Asp Pro Ala Tyr Leu Arg Gln Cys Leu
65                  70                  75                  80

Ala Ser Ala Arg Ala Leu Leu Tyr Pro Arg Ala Arg Val Arg Val Leu
                85                  90                  95

Met Val Val Asp Gly Asn Arg Ala Glu Asp Leu Tyr Met Val Asp Met
            100                 105                 110

Phe Arg Glu Val Phe Ala Asp Glu Asp Pro Ala Thr Tyr Val Trp Asp
        115                 120                 125

Gly Asn Tyr His Gln Pro Trp Glu Pro Ala Ala Gly Ala Val Gly
    130                 135                 140

Ala Gly Ala Tyr Arg Glu Val Glu Ala Glu Asp Pro Gly Arg Leu Ala
145                 150                 155                 160

Val Glu Ala Leu Val Arg Thr Arg Arg Cys Val Cys Val Ala Gln Arg
                165                 170                 175

Trp Gly Gly Lys Arg Glu Val Met Tyr Thr Ala Phe Lys Ala Leu Gly
            180                 185                 190

Asp Ser Val Asp Tyr Val Gln Val Cys Asp Ser Asp Thr Arg Leu Asp
        195                 200                 205

Pro Met Ala Leu Leu Glu Leu Val Arg Val Leu Asp Glu Asp Pro Arg
    210                 215                 220

Val Gly Ala Val Gly Gly Asp Val Arg Ile Leu Asn Pro Leu Asp Ser
225                 230                 235                 240

Trp Val Ser Phe Leu Ser Ser Leu Arg Tyr Trp Val Ala Phe Asn Val
                245                 250                 255

Glu Arg Ala Cys Gln Ser Tyr Phe His Cys Val Ser Cys Ile Ser Gly
            260                 265                 270

Pro Leu Gly Leu Tyr Arg Asn Asn Leu Leu Gln Gln Phe Leu Glu Ala
        275                 280                 285

Trp Tyr Asn Gln Lys Phe Leu Gly Thr His Cys Thr Phe Gly Asp Asp
    290                 295                 300

-continued

```
Arg His Leu Thr Asn Arg Met Leu Ser Met Gly Tyr Ala Thr Lys Tyr
305                 310                 315                 320

Thr Ser Arg Ser Arg Cys Tyr Ser Glu Thr Pro Ser Ser Phe Leu Arg
            325                 330                 335

Trp Leu Ser Gln Gln Thr Arg Trp Ser Lys Ser Tyr Phe Arg Glu Trp
                340                 345                 350

Leu Tyr Asn Ala Leu Trp Trp His Arg His Ala Trp Met Thr Tyr
            355                 360                 365

Glu Ala Val Val Ser Gly Leu Phe Pro Phe Val Ala Ala Thr Val
    370                 375                 380

Leu Arg Leu Phe Tyr Ala Gly Arg Pro Trp Ala Leu Leu Trp Val Leu
385                 390                 395                 400

Leu Cys Val Gln Gly Val Ala Leu Ala Lys Ala Ala Phe Ala Ala Trp
                405                 410                 415

Leu Arg Gly Cys Leu Arg Met Val Leu Leu Ser Leu Tyr Ala Pro Leu
                420                 425                 430

Tyr Met Cys Gly Leu Leu Pro Ala Lys Phe Leu Ala Leu Val Thr Met
            435                 440                 445

Asn Gln Ser Gly Trp Gly Thr Ser Gly Arg Arg Lys Leu Ala Ala Asn
    450                 455                 460

Tyr Val Pro Leu Leu Pro Leu Ala Leu Trp Ala Leu Leu Leu Leu Gly
465                 470                 475                 480

Gly Leu Val Arg Ser Val Ala His Glu Ala Arg Ala Asp Trp Ser Gly
                485                 490                 495

Pro Ser Arg Ala Ala Glu Ala Tyr His Leu Ala Ala Gly Ala Gly Ala
            500                 505                 510

Tyr Val Gly Tyr Trp Val Ala Met Leu Thr Leu Tyr Trp Val Gly Val
        515                 520                 525

Arg Arg Leu Cys Arg Arg Arg Thr Gly Gly Tyr Arg Val Gln Val
    530                 535                 540
```